US00PP20222P3

(12) United States Plant Patent
Klemm

(10) Patent No.: US PP20,222 P3
(45) Date of Patent: Aug. 18, 2009

(54) POINSETTIA PLANT NAMED 'NPCW07120'

(50) Latin Name: *Euphorbia pulcherrima*
Varietal Denomination: NPCW07120

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/004,185

(22) Filed: Dec. 20, 2007

(51) Int. Cl.
*A01H 5/00* (2006.01)

(52) U.S. Cl. ..... Plt./306

(58) Field of Classification Search ..... Plt./306
See application file for complete search history.

*Primary Examiner*—June Hwu
(74) *Attorney, Agent, or Firm*—Jondle & Associates, P.C.

(57) ABSTRACT

A new Poinsettia plant particularly distinguished by its compact, V-shape plant habit, strong stems, good branching and pink bracts is disclosed.

1 Drawing Sheet

Genus and species: *Euphorbia pulcherrima.*
Variety denomination: 'NPCW07120'.

BACKGROUND OF THE NEW PLANT

The present invention comprises a new and distinct cultivar of poinsettia plant, botanically known as *Euphorbia pulcherrima,* and hereinafter referred to by the cultivar name 'NPCW07120'. The new cultivar is the result of an induced mutation in the poinsettia plant 'NPCW02044' (U.S. Plant Pat. No. 14,618) made in the year 2005 in Stuttgart, Germany.

Plants of 'NPCW02044' were irradiated with x-rays in Stuttgart, Germany in 2005. The treated plants were grown in Stuttgart, Germany, and were propagated by shoot tip cuttings. The resulting plants were screened for positive mutations and examined during the flowering period in winter 2005/2006. Among these plants, a pink-flowered plant was selected and asexually multiplied for further examination in April 2006.

The new cultivar was created in 2005 in Stuttgart, Germany and has been asexually reproduced repeatedly by vegetative cuttings in Stuttgart, Germany over 6 generations. 'NPCW07120' has not been observed under all possible environmental conditions. The present invention has been found to retain its distinctive characteristics through successive asexual propagations.

Plant Breeder's Rights for this cultivar were applied for in Europe on Feb. 9, 2007. 'NPCW07120' has not been made publicly available more than one year prior to the filing of this application.

SUMMARY OF THE INVENTION

The following are the most outstanding and distinguishing characteristics of this new cultivar when grown under normal horticultural practices in Stuttgart, Germany.

1. A pink bract color;
2. A compact, V-shaped growth habit;
3. Strong stems; and
4. Very good branching.

DESCRIPTION OF PHOTOGRAPH

This new poinsettia plant is illustrated by the accompanying photograph which is an overhead view of the plant and shows bracts, flower buds, and the foliage of the plant; the colors shown are as true as can be reasonably obtained by conventional photographic procedures. The photograph is of a whole plant about months old grown in a greenhouse in Stuttgart, Germany, in November of 2007.

DESCRIPTION OF THE NEW CULTIVAR

The following detailed descriptions set forth the distinctive characteristics of 'NPCW07120'. The data which define these characteristics were collected from asexual reproductions carried out in Stuttgart, Germany. The plant history was taken on 4-month-old plants which were planted as rooted cuttings in 12-cm pots and were pinched in week 33. The plants were grown in a greenhouse under natural light. Color readings were taken under natural light in the greenhouse. Color references are primarily to the R.H.S. Colour Chart of The Royal Horticultural Society of London (R.H.S.) (2001).

DETAILED BOTANICAL DESCRIPTION OF THE NEW PLANT

Classification:
- *Family.*—Euphorbiaceae.
- *Botanical.—Euphorbia pulcherrima* (Willd. Ex Klotzsch).
- *Common name.*—Poinsettia.

Parentage:
X-ray induced mutation of the red-colored poinsettia plant 'NPCW02044' (U.S. Plant Pat. No. 14,618).

Growth:
- *Form.*—Shrub, self-branching, triangular.
- *Growth and branching habit.*—Upright, compact V-shaped growth habit; very good branching.
- *Height (from soil line to the top).*—20.0 cm to 25 cm.
- *Width.*—20.0 cm to 30.0 cm.
- *Time to produce a rooted cutting.*—About 20 days.
- *Time to produce a finished flowering plant.*—About 55 days.

*Keeping quality.*—About 25 days.

Branches:

*Average number.*—4 to 6.

*Length.*—20.0 cm.

*Internode length.*—1.0 cm to 4.0 cm.

*Diameter.*—30.5 cm to 1.0 cm.

*Stem color.*—Upper: RHS 143A. Lower: RHS 143A and RHS 183A.

Leaves:

*Quantity.*—8 to 15 per branch.

*Arrangement.*—Alternate.

*Size.*—Length: 4.0 cm to 10.0 cm. Width: 2.0 cm to 7.0 cm.

*Shape.*—Ovate.

*Margin.*—Entire.

*Apex.*—Acute.

*Base.*—Obtuse.

*Lobes.*—Slightly lobed.

*Color* (*mature leaves*).—Upper surface: RHS 139A. Lower surface: RHS 137B.

*Color* (*immature leaves*).—Upper surface: RHS 144B. Lower surface: RHS 143C.

*Texture* (*both surfaces*).—Smooth.

*Venation color.*—Upper surface: RHS 139A. Lower surface: RHS 139D.

*Variegation.*—None.

*Leaf petiole.*—Length: 2.0 cm to 4.0 cm. Diameter: 0.2 cm to 0.3 cm. Color: Upper surface: RHS 139A. Lower surface: RHS 137B. Texture: Smooth. Aspect: Horizontally directed, leaf blades slanting somewhat downward.

Bracts:

*Number per inflorescence.*—6 to 8.

*Shape.*—Ovate.

*Apex.*—Acute.

*Base.*—Obtuse.

*Lobes.*—Slightly lobed.

*Size.*—Length: 7.0 cm to 10.0 cm. Width: 4.0 cm to 6 cm.

*Texture.*—Smooth.

*Bract Color* (*both surfaces*).—RHS 58C.

*Vein color* (*both surfaces*).—RHS 58C.

*Bract Petiole.*—Length: 1.0 cm to 3.0 cm. Diameter: 0.2 cm. Color: RHS N66C to RHS N66D.

Inflorescence:

*Blooming habit.*—Blooms from November to January.

*Inflorescence type.*—Medium size, flat with the bracts mostly horizontally directed, in the center a tight cyme with medium size cyathia.

*Average number of inflorescences.*—4 to 6.

*Lastingness.*—About 4 to 5 weeks with no dropping of bracts.

*Diameter.*—15.0 cm to 20.0 cm.

*Height.*—2.0 cm to 5.0 cm.

Cyme:

*Cyme diameter.*—1.5 cm to 2.5 cm.

*Cyathia number.*—4 to 7 per inflorescence.

*Cyathium.*—Shape: Ovate. Diameter: 0.3 cm to 0.5 cm. Length: 0.4 cm to 0.7 cm. Color: RHS 143C.

*Peduncle.*—Color: RHS 143C. Length: 0.1 cm to 0.2 cm.

*Nectar cups.*—Number: One per cyathium. Size: Up to 0.3 cm wide. Color: RHS 14C.

Reproductive organs:

*Stamens.*—Number: 5 to 10 per cyathium. Shape: Ovate. Filaments: Color: RHS 58C. Length: 0.25 cm. Pollen: Quantity: Moderate. Color: RHS 9A to RHS 12A.

*Gynoecium.*—Present. Pistil number: 1 per cyanthia. Pistil length: 0.3 cm to 0.5 cm. Stigma shape: Two-parted (forked).

Fruit and seed set: No seed set observed so far.

Disease and insect resistance: The new poinsettia plant 'NPCW07120' is especially resistant to Botrytis. No particular insect resistance is observed.

COMPARISON WITH PARENTAL AND COMMERCIAL CULTIVARS

'NPCW07120' differs from the parental cultivar 'NPCW02044' (U.S. Plant Patent 14,618) by having pink instead of red bract color.

'NPCW07120' differs from the commercial cultivar '490 Pink' (U.S. Plant Pat. No. 8,817), by having less vigor, a longer response time and smaller foliage than '490 Pink'.

I claim:

1. A new and distinct cultivar of Poinsettia plant as shown and described herein.

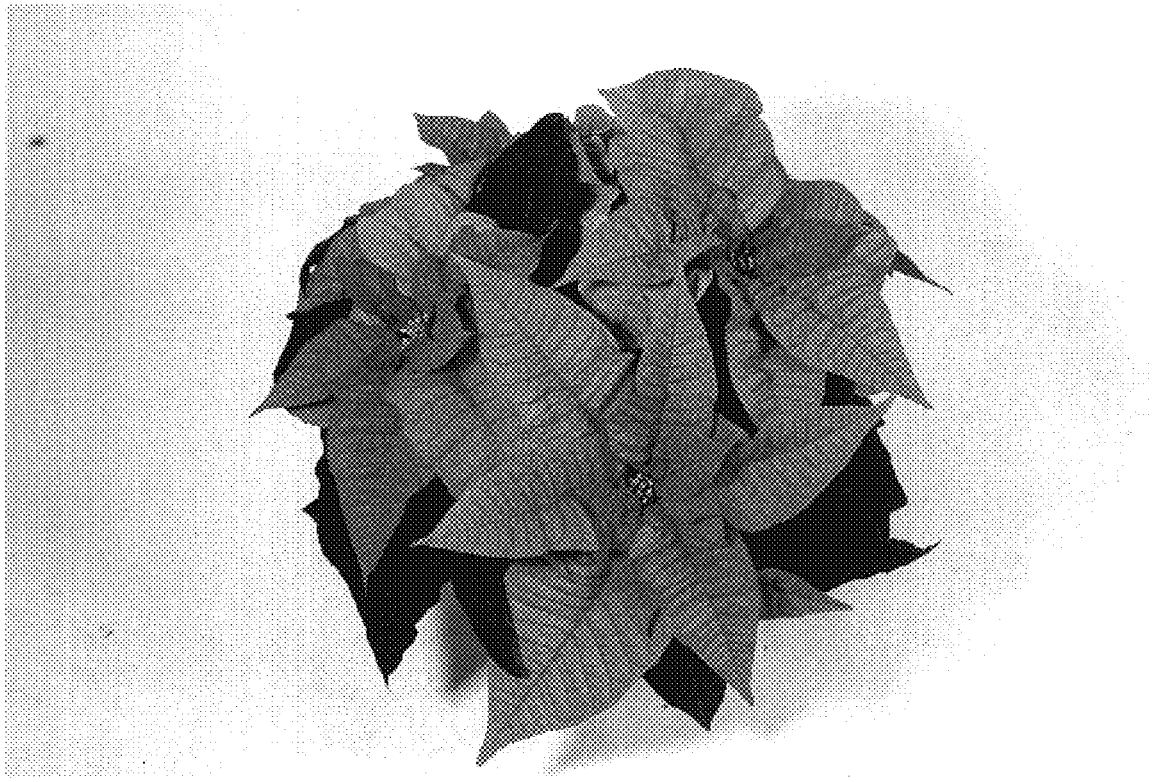

* * * * *